United States Patent [19]

Gordon et al.

[11] 4,324,239

[45] Apr. 13, 1982

[54] SAFETY VALVE FOR PREVENTING AIR EMBOLISM AND HEMORRHAGE

[75] Inventors: Marvin Gordon, East Windsor; Joseph Lichtenstein, Colonia, both of N.J.

[73] Assignee: Whitman Medical Corp., Clark, N.J.

[21] Appl. No.: 161,308

[22] Filed: Jun. 20, 1980

[51] Int. Cl.³ ............... A61M 5/00; F16L 29/00
[52] U.S. Cl. ............... 128/214 R; 128/349 R; 128/274; 251/149.6
[58] Field of Search ............... 128/214, 348, 349 B, 128/349 BV, 274; 251/149.6, 339, 347; 141/291, 296

[56] References Cited

U.S. PATENT DOCUMENTS

| | | | |
|---|---|---|---|
| 2,693,801 | 11/1954 | Foreman | 128/214 |
| 3,087,492 | 4/1963 | Garth | 128/350 R |
| 3,105,511 | 10/1963 | Murphy, Jr. | 137/399 |
| 3,399,677 | 9/1968 | Gould et al. | 251/149.6 X |
| 3,538,950 | 11/1970 | Porteners | 251/149.6 X |
| 3,570,484 | 3/1971 | Steer | 128/214 |
| 3,923,065 | 12/1975 | Nozick et al. | 128/349 B |
| 3,965,910 | 6/1976 | Fischer | 128/349 R |

*Primary Examiner*—Stephen C. Pellegrino
*Attorney, Agent, or Firm*—Holman & Stern

[57] ABSTRACT

A safety valve for catheterization procedures is characterized by a piston having an internal flow path, a portion of the piston being surrounded by an elastomeric member which surrounds a portion of the piston and biases it to a closed position. The elastomeric member also severely restricts fluid flow around the piston to eliminate any flow path other than the internal piston flow path.

10 Claims, 2 Drawing Figures

SAFETY VALVE FOR PREVENTING AIR EMBOLISM AND HEMORRHAGE

TECHNICAL FIELD

The present invention relates to a valving apparatus and method employed in a catheter arrangement to prevent entry of air into a patient's circulatory system and to prevent uncontrolled hemorrhaging.

BACKGROUND OF THE INVENTION

During various medical catheterization procedures, such as cardiac catheterization, central venous catheterization for parenteral nutrition, arterial catheterization, etc., there is a severe danger of a fatal air embolism and/or uncontrolled hemorrhaging. Such serious consequences can occur during the process of catheter insertion when the syringe is removed in order to thread the catheter, or during tubing changes, or if the intravenous tubing becomes inadvertently detached from the intravenous catheter, or after the catheter has been withdrawn and before the tract seals.

Attempts to prevent inadvertent separation of the tubing have included taping the components together or physically forcing them into one another; however, these attempts have not solved the problem and, in fact, sometimes result in air leaks by fracturing the hubs. In addition, certain safety valve arrangements have been attempted, such as those described in U.S. Pat. Nos. 2,693,801 (Foreman); 3,105,511 (Murphy); 3,399,677 (Gould et al); and 3,570,484 (Steer et al). In each of these devices the mechanism which actuates valve closure to provide the safety feature is disposed in the flow path of the administered fluid. Any tendency of the fluid to agglomerate on the mechanism compromises the safety feature. Moreover, such valves as disclosed in the aforementioned references, tend to be sufficiently complex and expensive as to render them less than ideal for disposability after use in a single procedure; lack of disposability, on the other hand, requires that the valve be cleaned and resterilized before each use. Further, it is questionable as to whether or not the valves in the afornementioned patents are sufficiently fast-operating to preclude a sudden explosive burst of air from entering the patient's vascular system during the valve closure interval.

SUMMARY OF THE INVENTION

It is a primary object of the present invention to provide a safety valve which is readily inserted in a central venous catheterization line (such as would be used for parenteral nutrition) and which precludes occurrence of an air embolism while the valve is closing as well as after the valve is closed. It is a further object of the present invention to provide such a safety valve for use in any vascular injection arrangement and which prevents air embolism and/or hemorrhage. It is another object of the present invention to provide a valve of the type described which is inexpensive and simple to manufacture yet reliable in operation.

In accordance with the present invention, the bias force for effecting closure in a safety valve is provided by an elastomeric material which also serves the function of diffusing or blocking sudden fluid flow through the valve chamber around the normal valving mechanism. The valve includes a piston arranged to reciprocate longitudinally in the valve chamber while opposite ends of the piston project into inlet and outlet openings of the chamber. A flange, in the form of a flat disc, surrounds the piston and extends radially therefrom in the chamber. The elastomeric material likewise surrounds the piston and fills the valve chamber on one side of the flange, the material being arranged to bias the piston toward the inlet end of the chamber. The piston is hollow and has an open inlet end, a closed outlet end, and outlet slots defined through the cylindrical wall of the piston proximate the outlet end. When biased fully toward the inlet end, the piston is disposed such that the outlet slots are blocked with respect to the valve outlet. In use, a male adaptor of a catheter tube is forced into the valve inlet end where it is held by frictional engagement. In this position, the tube adaptor is inserted into the open end of the piston and pushes the piston toward the outlet end of the valve chamber against the opposing force of the elastomeric material which is thereby compressed. This pushes the piston outlet slots to a position wherein they are no longer blocked and permits fluid to pass through the valve from the catheter tube via the piston interior. Should the adaptor become dislodged from its friction fit, the resilience of the elastomeric material acts on the flange to force the piston back toward the inlet end of the chamber into a position wherein the outlet slots are blocked. Importantly, the elastomeric material is of a type which blocks or severely restricts flow of fluids therethrough so that sudden air flow into the patient's vascular system by air trapped in the chamber around the outside of the piston is prevented.

BRIEF DESCRIPTION OF THE DRAWINGS

The invention will be better understood by referring to the accompanying drawings in which.

DESCRIPTION OF THE PREFERRED EMBODIMENT

Figure 1:
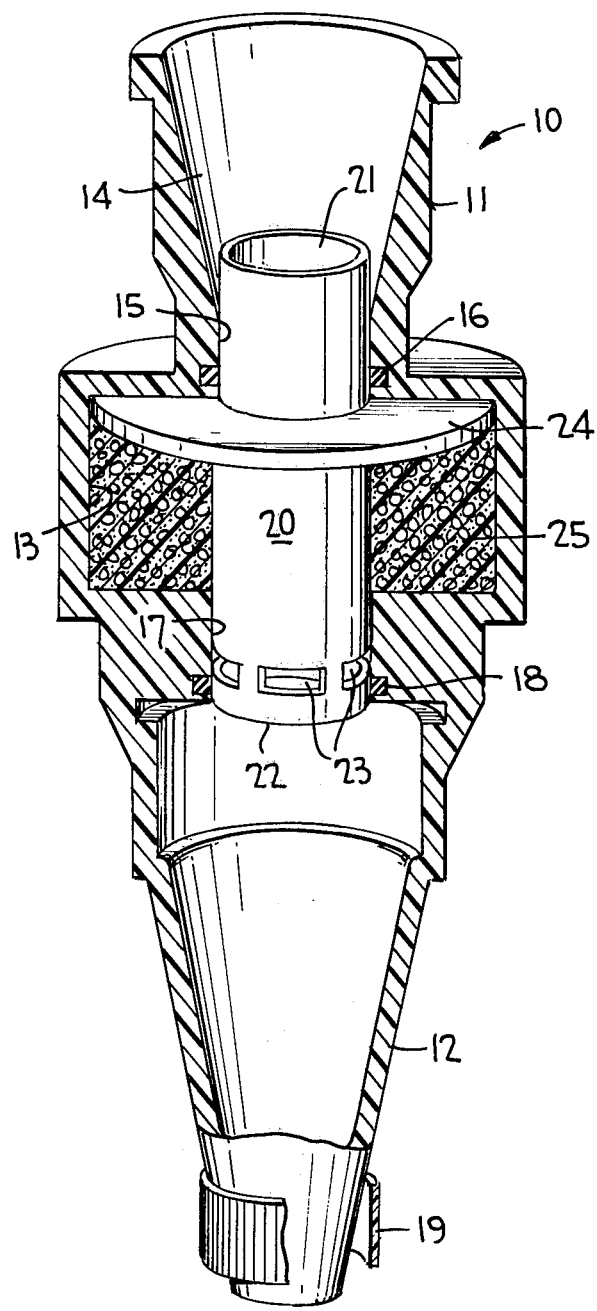
FIG. 1 is a plan view in section of a preferred embodiment of the present invention illustrating the valve in a closed position.

Referring more specifically to the drawings, the valve 10 of the present invention includes an inlet section 11 and an outlet section 12 separated by a valve chamber 13. Inlet section 11 includes a generally conical portion 14 which tapers or narrows towards valve chamber 13. Conical portion 14 terminates in an annular wafe 15 which defines an inlet opening to valve chamber 13. An O-ring 16 or the like is disposed in a suitably provided annular notch in wall 15. Inlet section 11 is arranged to receive and frictionally engage a male adaptor 30 of a catheter tube in a tight fit engagement.

Outlet section 12 includes an annular wall 17 which defines the outlet opening from chamber 13. An O-ring 18 or the like is disposed within a suitably provided annular notch in wall 17. The portion of outlet section 12 downstream of wall 17 tapers in a generally conical manner to a diameter suitable for connection to a catheter tube by means of a Luer lock 19 or the like.

Valve chamber 13 is generally cylindrical in the illustrated embodiment, but this configuration is by no means a limiting factor of the invention. The chamber inlet opening, defined by wall 15, and the chamber outlet opening, defined by wall 17, are generally aligned and sized to permit a piston 20 to slide longitudinally therethrough. Piston 20 has an open inlet end 21 and a closed outlet end 22. A plurality of outlet slots 23 are defined through the piston wall proximate outlet end 22 so as to define a flow path from open inlet end 21 through the piston interior, and out through slots 23. The outer periphery of piston 20 is sized to provide a pressure seal contact with each of O-rings 16,18 while permitting the piston to freely slide within those O-rings. A disc-like flange 24, preferrably formed integrally with the piston, surrounds the piston and extends radially therefrom in the valve chamber 13. Disc 24 is larger than either the inlet opening 15 or outlet opening 17 of the valve chamber and thereby retains the piston in the chamber.

The region of valve chamber 13 between disc 24 and outlet opening 17 is filled with an elastomeric material 25 which surrounds piston 24. Material 25, in the embodiment shown, is generally doughnut-shaped so as to entirely fill the valve chamber portion below flange 24. Of course, if chamber 13 is not cylindrical, the shape of material 25 should be changed accordingly. Material 25 is sufficiently resilient to exert sufficient force on flange 24 to bias the piston and flange toward chamber inlet 15 to the position illustrated in FIG. 1. This is defined as the closed position of the valve. It is noted that, in this position, the flange 24 abuts the inlet end of the valve chamber 13 while inlet end 21 of the piston 20 projects through inlet opening 15 into region 14. The outlet end 22 is disposed such that outlet slots 23 are blocked from communication with outlet section 12 by outlet wall 17 and O-ring 18. Material 25 must be able to perform this biasing function while serving to block, or at least severely restrict, the flow of liquids and gases through the chamber, even in the closed position of the valve (FIG. 1) wherein the material is expanded. Elastomeric materials of this nature are quite well known, examples of such comprising cellular or noncellular material or synthetic rubbers or plastics, such as highly dense or closed cellular polyurethane, styrene butadenes, isoprenes, and the like.

Figure 2:
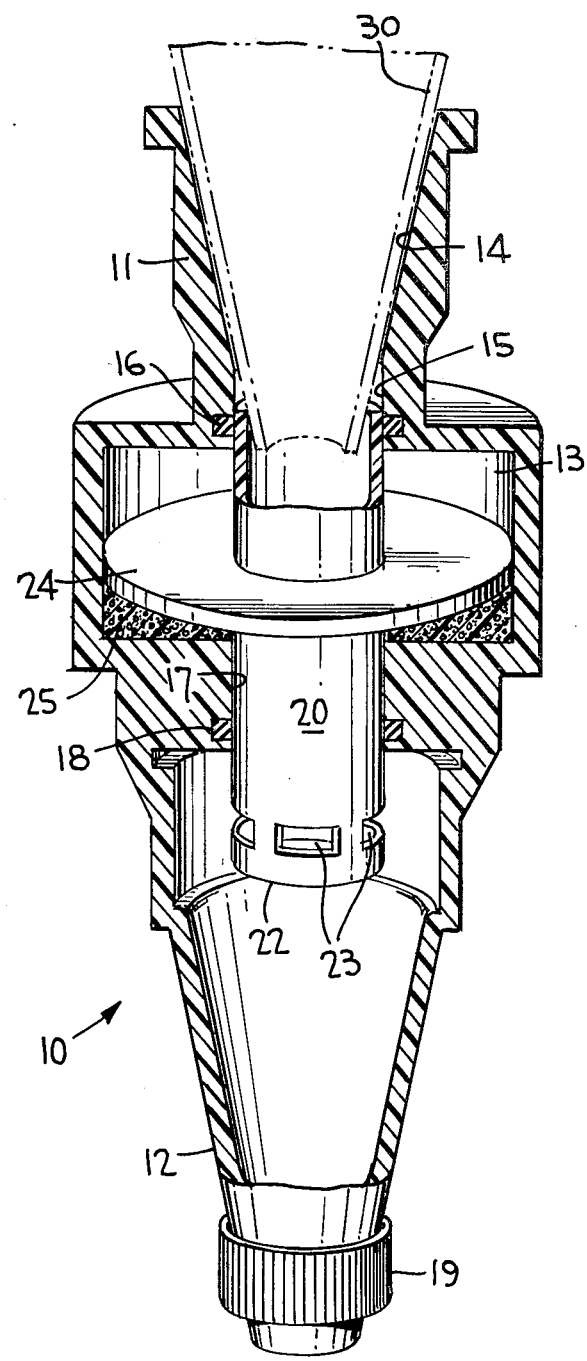
FIG. 2 is a view similar to that of FIG. 1, but illustrating the valve in an open position.

In use, as illustrated in FIG. 2, the adaptor 30 of a catheter tubing is inserted into inlet section 11 until firmly wedged or friction engaged in conical portion 14. In this position the tip of the adaptor is inserted into inlet opening 21 of piston 20 and forces the piston into chamber 13 against the biasing action of resilient material 25. Specifically, flange 24 compresses material 25 as it is urged into chamber 13 by the frictionally engaged adaptor 30. In this position, outlet slots 23 extend beyond chamber outlet 17 and into valve outlet section 12 so that fluid being administered can flow from adaptor 30 through piston 20 and out through outlet section 12 to the attached catheter tube. This is the open position of the valve. If the adaptor should become dislodged, either accidentally or intentionally during a tubing change, the adaptor 30 will no longer push the piston against the bias force of material 25. This material therefore returns the piston to the closed position of FIG. 1 wherein outlet slots 23 are blocked from communication with outlet section 12 of the valve.

It should be noted that in any valve position, material 25 precludes the existence of a flow path between chamber inlet 15 and chamber outlet 17 around the outside of the piston. That is, material 25, being closed cell or very dense open cell material, blocks or severely restricts fluid flow through the chamber position it fills. Thus, if the adaptor 30 is dislodged, an initial inrush of air thought the main valve flow path (i.e. through piston 20) is precluded while the valve is closing because of the supply fluid remaining therein immediately after the adaptor 30 is removed. In addition, the resilient material precludes air trapped in the valve from flowing around the piston to the outlet section. Thus, the valve positively precludes air embolism. Likewise, the valve precludes uncontrolled hemorrhaging by virtue of the same main valve path safety closure and the blockage or restriction provided by material 25. Thus, not only is the valve useful for central venous catheterization to provide parenteral nutrition, but is is also useful as a diagnostic gate to permit multiple blood withdrawals from an artery or vein without fear of uncontrolled hemorrhaging.

It is noted that the valve as described, has no obstructions in the main valve path which would collect residual blood clotting or block intravenous fluid.

The size of disc-like flange 24 should be as large as possible to provide as large a possible surface over which the bias force of material 25 can act. In addition, flange 24 should be as thin as possible without sacrificing rigidity, so that the mass of the piston and flange is minimized whereby the speed of valve response is maximized. Of course, the limitation of flange size is the contour of chamber 13; that is, the edges of flange 24 should not contact the chamber wall because the resulting drage would slow valve response.

O-rings 16,18 may be dispensed with if the material used for piston 20 and walls 15,17, and the sizes of the piston and these walls are selected to provide the necessary fluid sealing while permitting sufficient freedom for the piston to slide in these walls. In this regard, teflon may be a suitable material for walls 15 and 17.

The instant invention is not to be limited to the exact details of construction shown and described, for obvious modifications can be made by a person skilled in the art.

The embodiments of the invention in which an exclusive property or privilege is claimed are defined as follows:

1. An improvement in safety valves of the type used in catheterization procedures wherein a valve chamber includes a piston which is reciprocable between two positions in said chamber by means of a resilient bias member which urges the piston to a first of said two positions in which the valve is closed and by means of a connection to a fluid conduit which urges said piston to a second of said two positions wherein said valve is open, said improvement comprising:
    an internal flow path in said piston including means responsive to said piston being in said second position for freely conducting flow through said piston;
    means for blocking flow through said internal flow path when said piston is in said first position;
    and wherein said bias member comprises elastomeric flow restrictive means surrounding a portion of said piston in said chamber for at least severely restricting flow through said chamber around said piston.

2. The valve according to claim 1 wherein said elastomeric flow restrictive means is made of rubber.

3. The valve according to claim 1 wherein said elastomeric flow restrictive means is made of highly dense plastic material.

4. The valve according to claims 1, 2 or 3 wherein said connection to a fluid conduit comprises a generally conical receiving section for frictionally engaging an end of a catheter tube.

5. A safety valve for use in administering fluid into and withdrawing fluid from a patient, said valve comprising:
- a valve chamber having first and second openings;
- a valve member positioned in said chamber, said valve member having and second ends projecting through and slidable within said first and second openings, respectively, said valve member having an inlet opening at said first end, an outlet opening proximate said second end and an internal flow path between said inlet and outlet openings;
- retainer means projecting transversely from said valve member in said chamber for preventing removal of said valve member from said first and second openings while defining first and second extreme positions of said valve member in said chamber, said retainer means defining a sub-chamber in said valve chamber which sub-chamber is disposed between said retainer means and said second opening and changes in volume as the valve member slides;
- closure means for preventing fluid flow through said outlet opening when said valve member is in said first position and permitting such flow when said valve member is in said second position;
- bias means disposed in said valve chamber for biasing said valve member to said first position, said bias means comprising a resilient elastomeric member located between said retainer means and said second opening and comprised of a material which is at least severely restrictive to flow therethrough when in a relaxed state; and
- a valve inlet section including means for engaging a flow tube with the flow tube in communication with said inlet opening while forcing said valve member to said second position.

6. The valve according to claim 5 wherein said chamber is substantially cylindrical, wherein said valve member is a generally cylindrical piston, wherein said retainer means is an annular disc surrounding and projecting radially from said piston, and wherein said resilient member is a generally doughnut shaped member.

7. The valve according to claim 6 wherein said resilient member is made of rubber.

8. The valve according to claim 6 wherein said valve member is made of plastic.

9. A safety valve for use in catheterization procedures comprising:
- a valve chamber having first and second openings;
- a movable member disposed in said chamber;
- means for constraining said movable member to move between first and second positions in said chamber;
- a flow passage defined internally of said movable member and having inlet and egress openings;
- means for constraining said inlet opening into permanent flow communication with said first chamber opening for all positions of said movable member;
- means responsive to insertion of a fluid conduit into said first chamber opening for forcing said movable member to said second position;
- means for blocking flow through said egress opening in said first position of said movable member;
- means for conducting flow from said egress opening out through said second chamber in said second position of said movable member; and
- bias means for continuously moving said movable member toward said first position, said bias means comprising an elastomeric member made of material which is at least severely restrictive to flow therethrough, said elastomeric member being disposed in said chamber to surround said movable.

10. The safety valve according to claim 9, wherein said bias means further comprises a flange projecting from said movable member to sub-divide said chamber into first and second compartments which vary in volume with positional changes of the movable member in the chamber, said first compartment communicating directly with said first chamber opening, said second compartment communicating directly with said second chamber opening, and wherein said elastomeric member entirely fills the volume of said second compartment surrounding said movable member.

* * * * *